United States Patent [19]

Fradet

[11] Patent Number: 5,039,611
[45] Date of Patent: Aug. 13, 1991

[54] MONOCLONAL ANTIBODIES TO SUPERFICIAL PAPILLARY BLADDER TUMOR CELLS

[75] Inventor: Yves Fradet, Sillery, Canada

[73] Assignee: Universite Laval, Canada

[21] Appl. No.: 102,170

[22] Filed: Sep. 28, 1987

[30] Foreign Application Priority Data

Jun. 25, 1987 [CA] Canada .................................. 540486

[51] Int. Cl.$^5$ ........................ C12N 5/12; C07K 15/28
[52] U.S. Cl. .............................. 435/240.27; 530/387; 530/808; 935/104
[58] Field of Search .................. 530/387; 435/240.27; 935/95, 104

[56] References Cited

FOREIGN PATENT DOCUMENTS 0118891 9/1984 European Pat. Off. .

OTHER PUBLICATIONS

Duncan et al. (1984) Anal. Biochem. 112, 195–203.
Shulman et al. (1978) Nature (London) 276, 269–270.
Hsu et al. (1981), J. Histochem. Cytochem. 29, 577–580.
H. Ben-Aissa et al., "Specificites and Bindings Properties of 2 Monoclonal Antibodies Against Carcinoma Cells of the Human Urinary Bladder", Br. J. Can., 52:65–72 (1985).
Huland et al., "Human Transitional Cell Carcinoma in the NMRI-nu/nu Mouse Bladder: A New Animal Model for the *In Vivo* Use of Monoclonal Antibodies and Cytotoxic Agents", Can. Res. 46:2488–89 (1986).
Frodet et al., "Polymorphic Expression of a Human Superficial Bladder Tumor Antigen Defined by Mouse Monoclonal Antibodies", Proc. Natl. Acad. Sci.; 84:7227–7231 (1987).
Anal. Biochem., Duncan et al., (1984), 138:144–145.
Nature, Shulman et al., (1978), 276:269–270.
J. Histochem. Cytochem., Hsu et al., (1981), 29:577–580.
Proc. Natl. Acad. Sci. U.S.A., Fradet et al., (1984), 81:224–228.
Cancer Research, Lin and Prout, (1985), 45:5070–5079.
J. Exp. Med., Ueda et al., (1979), 150:564–579.
Anal. Biochem., Burnette, (1981), 112:195–203.

*Primary Examiner*—Esther L. Kepplinger
*Assistant Examiner*—Susan L. Futrovsky
*Attorney, Agent, or Firm*—Dressler, Goldsmith, Shore, Sutker & Milnamow, Ltd.

[57] ABSTRACT

There is provided four distinct hybrid cell lines bearing numbers M75, M300, M344 and 19A211, each producing a different monoclonal antibody of class lgG1, each antibody when used alone or in combination with one or more of the other three antibodies being capable of selective binding with one or more distinct antigens produced by superficial papillary bladder tumors of the human urinary bladder. There is also provided a method for producing such cell lines as well as a method and a test kit for the detection of distinct antigens produced by superficial papillary bladder turmors of the human urinary bladder. Provision is also made for use in flow cytometry (single or multiple laer) and in biosensors for detect of these antigens.

3 Claims, No Drawings

MONOCLONAL ANTIBODIES TO SUPERFICIAL PAPILLARY BLADDER TUMOR CELLS

BACKGROUND OF THE INVENTION

Low grade papillary superficial bladder tumors are the most common form of transitional cell carcinoma and current trends indicate that their prevalence is increasing. Although rarely progressing toward infiltration and metastasis, these tumors have a high recurrence rate and their detection by urine cytology is difficult because of the normal light microscopic appearance of the cells and their normal DNA content. This tumor type appears fairly distinct from the most aggressive carcinomas, although some overlapping and continuity clearly exists. It has been suggested that they represent two separate diseases.

Serological characterization of bladder cancer phenotypes with monoclonal antibodies has revealed a high degree of antigenic diversity. Most antigens are markers of the normal urothelial differentiation lineage or are acquired at a late stage of tumor progression. Studies have failed, however, to identify specific antigens of well-differentiated tumors, possibly due to the close resemblance of these cells to their normal counterpart.

The analysis of human bladder cancers with monoclonal antibodies has progressed rapidly in recent years, and several determinants on proteins or glycolipids have been recognized. In most previous studies, antibodies were obtained after immunization and screening on cultured cells and all antibodies described were reactive with human cancer lines.

In the few studies where antigen phenotype was correlated with tumor histologic grade and stage, the expression of antigens with apparent tumor specificity, not expressed on normal urothelium, was limited to the most advanced cancers. Om5 antigen was found to be the most restricted antigen with specificity for tumors of urothelial origin, particularly the superficial tumors. However this antigen, defined by monoclonal antibodies obtained from immunization with extracts of well-differentiated bladder tumor cells, was also expressed on normal urothelium of 55% of individuals tested.

Identification of unique antigens of human tumor cells in adult tissues has remained difficult despite the advent of hybridoma technology. One may question the existence of such antigens, or else the limits of the mouse immune repertoire. However an alternative explanation may be found in antigenic competition, which has long been recognized as one of the reasons for limited antibody production against antigen mixtures. This phenomenon may be particularly important when attempting to raise specific antibodies against tumor cells that retain much of the differentiated phenotype of their tissue of origin, so that tumor-specific antigens represent a very small minority of the total antigens.

Therefore the production of a monoclonal antibody defining an antigen restricted to superficial bladder tumors and non-reactive with normal urothelial cells would be highly desirable.

SUMMARY OF THE INVENTION

In accordance with the present invention, there is provided four distinct hybrid cell lines bearing numbers M75, M300, M344 and 19A211, each producing a different monoclonal antibody of class IgG1, each antibody when used alone or in combination with one or more of the other three antibodies being capable of selective binding with one or more distinct antigens produced by superficial papillary bladder tumors of the human urinary bladder.

Furthermore, there is provided a process for constructing hybrid cell lines for producing the above-mentioned monoclonal antibodies, which comprises the steps of immunizing mice with either superficial papillary bladder tumor cells and mouse polyclonal serum produced against normal human urothelial cells when monoclonal antibodies M75, M300 and M344 are desired or with normal human urothelial cells, superficial papillary bladder tumor cells and mouse polyclonal serum produced against normal human urothelial cells when monoclonal antibody 19A211 is desired; removing the spleens from the immunized mice and making a suspension of the spleen cells; fusing the removed spleen cells with mouse myeloma cells in the presence of a suitable fusion promoter; diluting and culturing the fused cells in separate wells in a medium which will not support the unfused cells; evaluating the supernatant in each well containing a hybridoma for the presence of antibody using indirect immunofluorescence and selecting and cloning hybridomas producing antibodies which react with one or more distinct antigens produced by superficial papillary bladder tumors of the human urinary bladder.

There is also provided a method for the detection of specific antigens produced by superficial papillary bladder tumors of the human urinary bladder, which comprises;

a) providing one or more mouse monoclonal antibodies of the IgG class and produced by one or more mouse lymphocytemyeloma hybridoma cell lines and capable of specifically binding to specific antigens produced by superficial papillary bladder tumor cells of the human urinary bladder, the antibody being attached to a solid phase;

b) contacting a fluid containing the targetted antigens with the solid phase to which the antibody or antibodies is bound under conditions to permit an immunological reaction between the antigens and the antibody or antibodies;

c) separating the unreacted fluid sample from the solid phase;

d) contacting the solid phase with a labelled second antibody capable of binding to the antigen which may be bound to the solid phase under conditions to permit an immunological reaction between the second antibody and the bound complexes;

e) separating unreacted second antibody from the solid phase, and f) detecting and/or determining the label on either the solid phase or the unreacted second antibody and relating this detection or determination to the presence or quantity of antigen in the fluid sample.

There is also provided an alternative method for assaying the presence of antigens to human papillary bladder tumor cells in a sample of test material, said method comprising:

a) binding the test material to an adsorptor substrate;

b) exposing the test material to at least one of the monoclonal antibodies produced by the hybridomas HB9678, HB9679 to allow the antibody to bind to the targetted antigen;

c) removing the unbound portion of the monoclonal antibodies, and d) assaying for the presence of bound-monoclonal antibodies.

Finally, there is provided a kit for determining the presence of one or more antigens produced by cells from superficial papillary bladder tumors in a sample wherein the antigen exists in the form of an immune complex. Such a kit comprises the following elements:

a) a solid support which binds an antibody;

b) a container holding a dissociating buffer containing the targetted antigens;

c) a container holding one or more antibodies capable of filling-in unoccupied sites on the solid support, and d) a container holding a labelled antibody, the support, buffer, antibody and labelled antibody being present in amounts sufficient to perform an assay for specific antigens to superficial human papillary bladder tumor cells.

Alternatively, the kit may comprise the following elements:

a) a solid support which binds the targetted antigen;

b) a container holding a dissociating buffer containing the targetted antigen, and c) a container holding one or more labelled antibodies capable of binding to the targetted antigen deposited on the support.

The four subject hybridomas and the antibodies produced thereby are identified herein by the designations M75, M300, M344 and 19A211. The subject hybridomas designated M344 and 19A211, respectively were deposited on Mar. 31, 1988 at the American Type Culture Collection, 12301 Parklawn Drive, Rockville, Md. 20852, and were given the respective ATCC accession numbers HB9678, HB9678 and HB9679.

The preparation and characterization of the hybridomas and the resultant antibodies will be better understood by referring to the following description.

DETAILED DESCRIPTION OF THE INVENTION

TISSUES AND CULTURED CELLS

For the purposes of the present invention, normal adult tissues were obtained at autopsy from surgical pathology specimens, and fetal tissues from abortions. Human tumors were obtained fresh and/or as formalin-fixed paraffin-embedded sections from the Surgical Pathology Department. Fresh tissues were frozen in liquid nitrogen, embedded in OCT (optimal cutting temperature) compound and stored at $-70°$ C. Bladder tumor cell suspensions for immunizations and serological tests were prepared by mechanical dispersion. Normal urothelial cells were obtained by gently scraping off the mucosa of bladder specimens from cadaver kidney donors. The preparations contained 95% urothelial cells as verified by flow cytometry with the specific monoclonal antibody T16 described by Fradet et al. in (1984) Proc. Natl. Acad. Sci. U.S.A. 81,224–228. Cultured human cancer lines came from the collection of the Sloan-Kettering Institute, N.Y. except for the bladder cancer lines MGH-U3 and U4 which were kindly provided by C. W. Lin and G. Prout, Mass. General Hospital, Boston and bear the characteristics described in (1985) Cancer Res. 45, 5070–5079. Short-term cultures of normal human kidney epithelial cells and fibroblasts were established according to the techniques described by Veda et al. in (1979) J. Exp. Med. 150, 564–579. Tests were routinely performed to rule out mycoplasma contamination of cell lines.

PREPARATION OF THE HYBRID CELL LINES

The method of preparing the hybrid cell lines of the present invention generally comprises the following steps:

A. Immunizing a first series of mice with normal human urothelial cells. While it has been found that female BALB/c mice are preferred, it is contemplated that other mouse strains could be used. The immunization schedule and the amount of urothelial cells should be such as to produce useful quantities of polyclonal antibodies 3 immunizations at 15 day intervals with $1 \times 10^7$ urothelial cells has been found to be effective.

B. Preparing polyclonal antibody serum from the blood of the immunized mice.

C. Immunizing a second series of mice with either cells from well-differentiated papillary bladder tumors and the serum obtained in Step B, or with normal urothelium cells at the neonatal period and 6 weeks later with cells from well-differentiated papillary bladder tumors and the serum obtained in Step B. Again, while it has been found that female BALB/c mice are preferred, it is contemplated that other mouse strains could be used. The immunization schedule and the amounts of tumor cells and serum should be such as to produce useful quantities of suitably primed splenocytes. Three immunizations at 28 day intervals, one with $1 \times 10^7$ tumor cells and 150 $\mu$l of the serum of Step B and two with $1 \times 10^7$ tumor cells and 75 $\mu$l of the serum of Step B or one immunization with $1 \times 10^7$ cells form normal urothelium within 24 hours of birth followed 6 weeks and 10 weeks later by intraperitoneal injections of $1 \times 10^7$ cells from a papillary superficial bladder tumor, and followed 18 weeks later by the injection of $5 \times 10^6$ bladder tumor cells and the serum of Step B have been found to be effective.

D. Removing the spleens from the immunized mice of Step C and making a spleen suspension in an appropriate medium. The techniques related to this step are well-known by those skilled in the art.

E. Fusing the suspended spleen cells with mouse myeloma cells from a suitable cell line by the use of a suitable fusion promoter. A wide variety of mouse myeloma cell lines are known are readily available. The cell line used should preferably be of the so-called "drug-resistant" type, so that unfused myeloma cells will not survive in a selective medium, while hybrids will survive. The most common class is 8-azaguanine resistant cell lines which lack the enzyme hypoxanthine guanine phosphoribosyl transferase and hence will not be supported by HAT (hypoxanthine, aminopterin and thymidine/medium). It is also generally preferred that the myeloma cell line used be of the so-called "non-secreting" type, in that it does not itself produce any antibody. For the purposes of the present invention, non-secreting mouse myeloma SP 2/0-Ag 14 cells, a total non-producer variant selected from a hybridoma involving fusion of MOPC-21 and BALB/c spleen cells, provided excellent results. Although SP 2/0-Ag 14 is a non-secreting type of cell line, the use of secreting types can also be envisaged. Furthermore, while the preferred promoter is polyethylene glycol, other fusion promoters known in the art may be employed.

F. Diluting and culturing in separate containers, the mixture of unfused spleen cells, unfused myeloma cells, and fused cells in a selective medium which will not support the unfused myeloma cells for a time sufficient to allow death of the unfused cells. The dilution may be a type of limiting one, in which the volume of diluent is statistically calculated to isolate a certain number of cells in each separate container such as each well of a microtiter plate. The medium is one which will not support the drug resistant unfused myeloma cell line. For example, HAT medium will not support 8-azaguanine resistant myeloma cell lines. Hence, these myeloma cells perish. Since the unfused spleen cells are nonmalignant, they have only a finite number of generations. Thus, after a certain period of time which is usually about one week, these unfused spleen cells fail to proliferate. On the other hand, the fused cells continue to proliferate because they possess the malignant quality of the myeloma parent and the ability to survive in the selective medium.

G. Evaluating the supernatant in each container containing a hybridoma for the presence of antibody; and H. Selecting and cloning hybridomas producing the desired antibody.

I. Producing the desired antibody in substantial concentration. In order to produce a large concentration and quantity of monoclonal antibody, the desired hybridoma may be injected into host animals of the same species as those used to prepare the hybridoma, preferably syngenic or semisyngenic animals. Mice were used in the present invention. This injection is preferably into the peritoneum of the host. The hybridoma will cause formation of antibody-producing tumors in the host after a suitable incubation time, resulting in a very high concentration of the desired antibody (about 5–20 mg/ml) in the blood stream and peritoneal exudate (ascites) of the host. Although these hosts also have normal antibodies in their blood and ascites, the concentration of these normal antibodies is only about five percent of the concentration of the desired monoclonal antibody. Moreover, since these normal antibodies are not antihuman in their specificity, the monoclonal antibody obtained from the harvested ascites or from the serum is essentially free from any contaminating antihuman immune globulin. This monoclonal antibody is normally of high titer (active at dilutions of 1:100,000 or higher) and high ratio of specific to non-specific immune globulin (about 1/20 or greater).

In the practice of the subject method, specific antibodies M75, M300, M344 and 19A211 are isolated from the ascites fluid produced as described above by passing the fluid over a chromatography column which allows separation of these antibodies from contaminating materials.

METHOD FOR DETECTING ANTIGENS PRODUCED BY SUPERFICIAL PAPILLARY BLADDER TUMOR CELLS

Once monoclonal antibodies M75, M300, M344 and 19A211 are available in substantial concentrations, they may be used as diagnostic reagents for the detection of superficial papillary bladder tumors. In the method used for detecting antigens produced by superficial papillary bladder tumor cells the following steps are performed:

The antibody or a mixture of at least two antibodies selected from M75, M300, M344 and 19A211, is adsorbed onto a solid surface such as the surface of a polystyrene microtiter plate to form the solid phase needed in the subject method. Techniques for coating antibody or a mixture of antibodies onto solid surfaces are well-known in the art.

To the wells of this antibody-coated microtiter plate are added samples of the serum urine or cellular extracts to be tested, preferably diluted in buffer. The wells are preferably incubated to allow complete immunological reaction to occur, although such incubation is not essential for operation of this method. Following the incubation, the fluid in each well is then removed and the wells are washed to remove any remaining unreacted serum.

To detect the presence of antigens to superficial papillary bladder tumor cells coated onto the wells, it is preferred to use M344, 19A211 or a combination thereof labelled with an enzyme such as peroxidase. Methods of attaching labels to antibodies are well-known in the art. Although peroxidase is the preferred label for detecting the immune complex, other labels such as phosphatase alkaline may be contemplated. Furthermore, although enzyme is the preferred detector, other materials which would bind to the antigen complexes may also be employed.

After addition of peroxidase labelled M344 and 19A211 or combination thereof to the coated wells, the microtiter plates are preferably permitted to incubate to allow complete immunological reaction, although such incubation is not essential. Following the incubation, the unreacted second antibody is removed and the wells are washed to remove any remaining unreacted second antibody. The bound M344 and 19A211 label may then be detected by optical density. The presence of labelled second antibody and thus of the investigated antigen is indicated.

Alternatively, the antigen or a fluid containing the antigen such as urine or cellular extracts may be adsorbed onto a solid surface such as nitrocellulose, PVC or the surface of a polystyrene microtiter plate to form the solid phase needed in the subject method. Techniques for coating antigens onto solid surfaces are also well-known in the art. To the wells of this antigen-coated microtiter plate is added a solution containing a labelled antibody or a mixture of at least two labelled antibodies selected from M75, M300, M344 and 19A211. The wells are preferably incubated to allow complete immunological reaction to occur, although such incubation is not essential. Following the incubation, the fluid in each well is removed and the wells are washed to remove any remaining unreacted antibody. The bound labelled antibody may then be detected by the appropriate detection method.

TEST KIT FOR THE DETECTION OF ANTIGENS TO SUPERFICIAL PAPILLARY BLADDER TUMORS

The subject test kit comprises a suitable solid phase surface such as microtiter wells, beads, or the like having one or a mixture of selective superficial papillary bladder tumor antibodies attached thereto and a labelled second antibody capable of binding to the antigen-containing complex when it is bound to the antibody on the solid phase. The test kit may also include means for detecting the label or the second antibody as well as other materials used to practice the subject method.

Alternatively, the test kit may include a suitable solid phase onto which the targetted antigen may be adsorbed, and a mixture of labelled selective superficial papillary bladder tumor antibodies which bind to the adsorbed targetted antigen.

Although the above method has been described using detection of the bound, labelled second antibody as the measure of the bound antigen-containing complex, it should also be appreciated that it would be equally possible to determine the amount of unbound labelled second antibody in relation to the amount of second antibody added and to detect the presence of or determine the amount of bound antigen-containing complex from that calculation.

Thus, by passive immunization of mice against the dominant antigens of normal human urothelium, immunological reaction against these antigens is suppressed and simultaneous active immunization of the same mice with intact well-differentiated bladder tumor cells provided monoclonal antibodies able to recognize small quantities of highly restricted antigens common to a majority of superficial bladder tumors which have remained very difficult to detect by diagnostic cytology.

Therefore, the novel antibodies of the present invention may be used as diagnostic agents for superficial papillary bladder tumor cells. Furthermore, because the high stability of the binding sites of the antigens, these antibodies are also able to detect the antigens or fragments thereof in urine or other body fluids from dead bladder cells.

As other examples of diagnostic or investigation procedures for which the monoclonal antibodies of the present invention could be used, there may be mentioned the following:

Improvement of the sensitivity of the standard diagnostic urine cytology test by immunoperoxidase staining of the cells.

Distinction of normal diploid tumors from normal cells in flow cytometry studies.

In vivo targetting of tumor cells by intra-vesical instillation and subsequent lazer photolocalization and/or therapy.

Immunohistological studies of bladder tumors in routine surgical pathology.

Use in biosensors.

The synthesis processes and products of the present invention will be more readily illustrated by referring to the following examples which do not intend to limit the present invention thereto.

EXAMPLE 1

PRODUCTION OF M75, M300 AND M344 MONOCLONAL ANTIBODIES

A. Immunizations of mice

Female BALB/c mice (age 6 weeks) were immunized three times at intervals of 4 weeks by intraperitoneal inoculation of $1 \times 10^7$ cells from well-differentiated papillary bladder tumors. These mice were also simultaneously immunized with 150 µl initially and thereafter with 75 µl of serum prepared from the blood of another series of BALB/c mice which had been immunized 3 times at 15 day intervals with $1 \times 10^7$ normal human urothelial cells.

B. Cell fusion and cloning

Three days after the last injection, the mice spleens were removed and dissociated into single cell suspensions. The spleen cells were then fused with non-secreting cells from mouse myeloma line SP 2/0-Ag 14, as previously described by Shulman et al. in (1978) Nature (London) 276, 269–270, and then aliquoted into ten 96 well culture plates in HAT selective medium. After 14 days, hybridomas were present in approximately 50% microtiter wells. Fluid from each of the wells containing fast growing cells was assayed for bladder tumor cell antigen reactivity by indirect immunofluorescence. The fast growing cells were also tested for reactivity with normal urothelial cells attached to microplates with poly-L-lysine and fixed briefly with methanol:acetone 1:1. Among the 445 wells tested, 40 tested positive on the tumor cells and negative on the normal urothelial cells used for producing the immune serum. These hybridomas were cloned by limiting dilution and grown as ascites.

C. Hybridoma growth

The selected hybridomas were injected into BALB/c mice peritoneum previously injected wtih Prestane ®. Monoclonal antibodies M75, M300 and M344 were then purified from ascites fluid by two successive precipitations with 40% ammonium sulfate and separation by FPLC on a Pharmacia Mono Q column.

D. Antibody isotyping

Subclasses were determined by the Ouchterlony test. M75, M300 and M344 antibodies were all found to be of class $IgG_1$.

EXAMPLE 2

PRODUCTION OF 19A211 MONOCLONAL ANTIBODY

A. Immunizations of mice

Female BALB/c mice (age between 20 and 30 hours) were first immunized by introperitoneal inoculation of $1 \times 10^7$ cells from normal human urothelium. At the age of 6 weeks, the mice were then immunized by intraperitoneal injection of $1 \times 10^7$ cells from a papillary superficial bladder tumor. The latter immunization was repeated four weeks later. Finally, 8 weeks after the last bladder tumor cells immunization, a mixture of $5 \times 10^6$ bladder tumor cells and 150 µl of serum prepared from the blood of another series of BALB/c mice which had been immunized 3 times at 15 day intervals with $1 \times 10^7$ normal human urothelial cells was injected intraperitoneally to the mice.

B. Cell fusion, cloning, hybridoma growth and antibody isotyping

The steps were performed following steps B, C and D of Example 1. 19A211 monoclonal antibody was also found to be of class IgG1.

EXAMPLE 3

CHARACTERIZATION OF M75, M300, M344 AND 19A211 REACTIVITIES

A. Serological analyses

The binding specificity of M75, M300, M344 and 19A211 antibodies was first assessed by serological tests on cell lines using high concentrations of monoclonal antibodies purified from ascites. These tests included rosetting and indirect immunofluorescence assays on both viable cells and cells fixed with methanol:acetone 1:1. In studies on a large panel of urothelial cells and bladder tumor cells, the four antibodies reacted with several tumors but did not react with any normal urothelial cells. The cellular immunofluorescence pattern was granular, with frequent polarity suggesting capping and was similar for all four antibodies. As it can be seen in Table 1, thirteen bladder cancer lines, 29 cell lines from other origins, as well as EBV transformed lymphocytes and short-term cultures of fibroblasts and kidney epithelial cells did not react with any of the four above-mentioned monoclonal antibodies.

TABLE 1

Cultured human cells tested and non-reactive with monoclonal antibodies M75, M300, M344 and 19A211.

| Cancer cell line | Number tested | Type of cell |
|---|---|---|
| Bladder | (13) | SW780, MGH-U4, RT4, 5637, T24, VMCUB3, 639V, 647V, 253-J, SW1710, J.O.N., Scaber, SW800 |
| Lung | (3) | SKLC-5, SKLC-6, SKLC-13 |
| Prostate | (2) | DU-145, PC3 |
| Uterine | (1) | ME180 |
| Ovarian | (1) | ROAC |
| Teratocarcinoma | (1) | Tera-2 |
| Breast | (2) | MCF-7, BT-20 |
| Colon | (4) | SW1222, HT29, SW1417, SKCO-10 |
| Renal | (9) | SKRC-1, SKRC-2, SKRC-7, SKRC-18, SKRC-29, SKRC-39, SKRC-45, SKRC-48, Caki |
| Melanoma | (2) | SKMEL-28, SKMEL-37 |
| Astrocytoma | (4) | U-251, SKMG-1 SKMG-BQ, U373 |

| Normal cell line | Number tested | Type of cell |
|---|---|---|
| Fibroblasts | (3) | HDQFB-1, HDQFB-2, HDQFB-3 |
| Kidney epithelial cells | (7) | HDQNK-1 to -7 |
| EBV transformed lymphocytes | (2) | |
| Red blood cells A, B, O | | |

B. Immunohistological studies

Reactivity of M75, M300, M344 and 19A211 antibodies was further evaluated on tissue sections by the avidin:biotin:peroxidase method described by Hsu et al. in (1981) J. Histochem. Cytochem. 29, 577–580. In a first series of experiments, tests were performed on 5 μm portions of frozen tissue sections of both normal and tumoral tissues fixed in acetone at −20° C. for 10 minutes and blocked with 0.6% hydrogen peroxide for 30 minutes. A second series of tests were performed on formalin-fixed sections having been deparaffinized and rehydrated through successive incubations in toluene 100%, ethanol 100% and 95% phosphate buffer saline (PBS). Undiluted hybridoma culture supernatants (used as controls) were incubated for 1 hour on frozen sections and overnight on paraffin sections. A 3 minute wash with 0.01% Tween® 20 in PBS was added between each incubation to eliminate non-specific staining diaminobenzidine:hydrogen peroxide was used as the chromagen and sections were counterstained with hematoxylin. For each monoclonal antibody, both series of tests generated identical intensities on patterns of reactivity. Paraffin sections were therefore used for subsequent studies and no distinction was made in compiling data.

M75, M300 and M344 antibodies

The results of tests with M75, M300 and M344 monoclonal antibodies on non-urothelial normal adult and fetal tissues and on non-bladder tumor are summarized in Table 2. No reactivity was observed with any of 23 adult and fetal tissue types from several individuals. All 45 non-bladder tumor specimens studied were also negative, with the exception of one breast tumor which reacted with M344 only, with staining observed on the apical side of a few carcinoma cells but not on the normal breast elements.

TABLE 2

Reactivity of M75, M300, and M344 monoclonal antibodies by immunoperoxidase staining with non-urothelial human tissues, normal and tumoral

| Normal tissues | | | |
|---|---|---|---|
| Adult kidney | 0/10* | Breast | 0/6 |
| Fetal kidney | 0/4 | Lung | 0/4 |
| Prostate | 0/9 | Lymph node | 0/2 |
| Fetal prostate | 0/2 | Spleen | 0/3 |
| Seminal vesical | 0/1 | Thyroid | 0/1 |
| Skin & adnexae | 0/8 | Testicule | 0/2 |
| Oesophagous | 0/2 | Hypophysis | 0/1 |
| Stomach | 0/2 | Brain | 0/1 |
| Ileum | 0/1 | Heart | 0/2 |
| Colon | 0/5 | Aorta | 0/1˙ |
| Pancreas | 0/2 | Trachea | 0/1 |
| Liver | 0/3 | Prostate | 0/2 |
| Tumors | | | |
| Renal | 0/10 | Bladder condyloma | 0/1 |
| Breast | 1/6+ | Skin condyloma | 0/2 |
| Prostate | 0/3 | Molluscum | 0/2 |
| Colon | 0/4 | Skin cancer squamous | 0/3 |
| Lung | 0/4 | Basal cell | 0/2 |
| Ovarian | 0/2 | Melanoma | 0/2 |
| Endometrium | 0/1 | Meningioma | 0/1 |
| Lymphoma | 0/2 | | |

*Number positive over number of individuals tested.
˙ Different pattern with only one of the three monoclonal antibodies Furthermore, M75, M300 and M344 monoclonal antibodies did not react with any of 3 skin or bladder condylomas. As for other types of bladder tumors, the positive staining pattern was identical for all three monoclonal antibodies. Results are presented for M344 antibody selected as the prototype reagent. As shown in Table 3, M75, M300 and M344 monoclonal antibodies reacted with 30/44 superficial papillary or in situ tumors and with only 4/27 infiltrating tumors. However, in the latter instances, reactivity was observed on associated in situ lesions or superficial tumors and was not detected on the infiltrating areas of the tumors. Conversely, normal urothelium from 36 adults and 4 foetuses were negative, including urothelium from 13 individuals whose associated carcinoma in situ or superficial papillary tumors were positive. The cell in staining was always strong and unquestionable; however, there was much heterogeneity between specimens in the size of the antibody reactive cell population. Three patterns were generally observed: 6/30 positive superficial tumors were homogeneously stained (pattern I), in 12/30 heterogeneous reactivity was observed on approximately 50% of tumor cells (pattern II) and in 11/30, clusters of clearly positive cells were detected throughout the tissue section (pattern III).

Results of urine diagnostic cytology performed immediately before tumor resection were available in 34/40 patients with papillary superficial (Ta) tumors. Cytology was positive in only 5/34 (15%) patients. Of the 29 tumors not predicted by the cytology test, 20 (69%) were positive with M344 antibody.

TABLE 3

Reactivity of M344 antibody with normal urothelium and bladder tumors

| Tissue tested | Number of specimens tested | Number positive (%) | Patterns of positive reactivity with M344* | | |
|---|---|---|---|---|---|
| | | | I | II | III |
| Normal urothelium | | | | | |
| Adult | 36 | 0 | 0 | 0 | 0 |
| Fetal | 4 | 0 | 0 | 0 | 0 |
| From individuals with M344 positive tumors | 13 | 0 | 0 | 0 | 0 |
| Bladder tumors | | | | | |
| Carcinoma in situ (Tis) | 4 | 4(100) | 2 | 1 | 1 |
| Papillary superfic. (T$_a$) | 40 | 26(65) | 4 | 12 | 10 |
| Infiltrating tumors | | | | | |
| T$_1$ | 6 | 1(27) | 0 | 1 | 0 |
| T$_2$ | 7 | 2(29) | 0 | 1 | 1 |
| T$_3$ | 10 | 1(10) | 0 | 0 | 1 |
| T$_4$ | 4 | 0 | 0 | 0 | 0 |

*Patterns of reactivity: I-majority of the tumor cells strongly reactive; II-heterogeneity with more than 50% of tumor cells positive; III-clusters of positive cells.

M19A211 antibody

No reactivity was observed with a series of normal tissues from different individuals, as well as from tumors of non-urothelial origin with the exception of two skin papillomas that showed a strong staining with 19A211 antibody, but not the normal adjacent skin.

TABLE 4

Reactivity of 19A211 monoclonal antibody by immunoperoxidase staining with non-urothelial human tissues, normal and tumoral

| Normal tissues | | | |
|---|---|---|---|
| Adult kidney | 0/10* | Breast | 0/6 |
| Fetal kidney | 0/4 | Lung | 0/4 |
| Prostate | 0/9 | Lymph node | 0/2 |
| Fetal prostate | 0/2 | Spleen | 0/3 |
| Seminal vesical | 0/1 | Thyroid | 0/1 |
| Skin & adnexae | 0/8 | Testicule | 0/2 |
| Oesphagous | 0/2 | Hypophysis | 0/1 |
| Stomach | 0/2 | Brain | 0/1 |
| Ileum | 0/1 | Heart | 0/2 |
| Colon | 0/5 | Aorta | 0/1 |
| Pancreas | 0/2 | Trachea | 0/1 |
| Liver | 0/3 | | |
| Tumors | | | |
| Renal | 0/10 | Bladder condyloma | 0/1 |
| Breast | 0/6 | Skin condyloma | 2/2* |
| Prostate | 0/3 | Molluscum | 0/2 |
| Colon | 0/4 | Skin cancer squamous | 0/3 |
| Lung | 0/4 | Basal cell | 0/2 |
| Ovarian | 0/2 | Melanoma | 0/2 |
| Endometrium | 0/1 | Meningioma | 0/1 |
| Lymphoma | 0/2 | | |

*Number positive over number of individuals tested.

This antibody reacted with 32/63 bladder tumors of which the majority were of the papillary superficial (Ta) subtype. Only 25% of the normal urothelium tested were reacting with monoclonal antibody 19A211. In these instances, the staining was limited to the very superficial "umbrella" cells of the urothelium and was not found on the other layers. In nine instances, where the bladder tumor was positive with the antibody 19A211, the normal adjacent urothelium was negative. In two instances of negative tumors, the superficial cells of the urothelium were positive with 19A211. These results are summarized in Table 5.

TABLE 5

Reactivity of 19A211 antibody with normal urothelium and bladder tumors

| Tissue tested | Number of specimens tested | Number positive (%) |
|---|---|---|
| Normal urothelium | | |
| Adult | 23 | 6(26) |
| Fetal | 4 | 1(25) |
| From individuals with 19A211 positive tumors | 9 | 0 |
| Bladder tumors | | |
| Carcinoma in situ (Tis) | 5 | 4(80) |
| Papillary superfic. (T$_a$) | 38 | 24(63) |
| Infiltrating tumors | | * |
| T$_1$ | 4 | 0 |
| T$_2$ | 7 | 2(28) |
| T$_3$ | 7 | 1(14) |
| T$_4$ | 2 | 1 |

C. Biochemical and immunoblot studies

No reactivity was observed when M75, M300, M344 and 19A211 monoclonal antibodies were tested by hemagglutination with A, B, O, or neuraminidase-treated O (T-antigen) human erythrocytes or by solid-phase ELISA with purified blood group glycoproteins (antigens A, B, H, l, Le$^a$, Le$^b$, X and Y).

Considerable attention has been directed recently towards the occurrence of heterogeneity of antigenic expression in human tumors. Blood antigens are known for their marked heterogeneity of expression which frequently parallels tumor progression, and this has been extensively studied in bladder cancer. The pattern of expression of the M344 antigen does not correlate with any blood group phenotype, and direct testing on purified blood group antigens has not shown any reactivity. At least two general mechanisms could account for the marked variation in size of the tumor cell populations expressing the M344 antigen between tumors from different patients. Phenotypic heterogeneity may reflect genetic instability within various clones of cells, which could explain the loss of M344 antigen on more aggressive cancers but is less likely to play a role in well-differentiated tumors. Alternatively, the antigen may define a distinct class of tumors, and its expression be either at random or related to the growth or differentiation status of the cells.

Cell suspensions of bladder tumors and normal urothelium were extracted with 0.2% Ammonix detergent (is it commercially available) in 50 mM tris-HCl pH 8.0 containing 150 mM NaCl (TBS) for 1 hour. After centrifugation at 100,000 g for 1 hr. extracts were digested with DNAse 1 for 1 hr. on ice. Protein extracts (100 μg/sample) were electrophoresed on a 7.5-15 SDS:polyacrylamide gradient gel using Laemmli's buffer system (16). For two dimensional analysis, the proteins were first focussed in tube gels following the method of O'Farrel as modified by R. Duncan et al. in (1984) Anal. Biochem. 138, 144-145, and the second dimension was performed as above. The proteins were transferred onto nitrocellulose paper at 500 mA overnight following Burnettes' method which is described in (1981) Anal. Biochem. 112, 195-203. Unreacted sites on the nitrocellulose paper were blocked with 5% fat-free powdered milk in TBS for 2 hrs. The paper was then incubated with 20 μg/ml of purified mAbs diluted in 1% milk powder in TBS overnight at 4° C. After removal of unreacted antibody and further blocking, incubation was performed with $^{125}$I-labelled goat antimouse lg (New England Nuclear) diluted in the blocking solution for 2 hr. After thorough washing, the paper was dried and autoradiographed.

Most of the reactivity was found in the cytosol fraction. The antigen was relatively resistant to extraction from whole cells with 0.5% Nonidet P-40 or CHAPS detergents, but was easily extracted with 0.2% Ammonix or Sodium Dodecyl Sulphate. Proteinase K pretreatment of the extracts abolished the reactivity with the antibody, suggesting that the epitope may reside on a protein moiety. Immunohistological studies strongly suggested that the three monoclonal antibodies M75, M300 and M344 recognized the same antigen. This was confirmed by solid-phase inhibition assays where unlabelled monoclonal antibodies, M300 and M344 competed optimally, and M75 only to 45%, with binding of $^{125}$I-M300 to extracts from three different tumors. 19A211 did not compete with M300.

TABLE 6

| Competing unlabelled IgG1 monoclonals | Solid-phase inhibition assays Percent inhibition of binding of $I^{125}$-labelled M300 antibody tumor lysates from patients | | |
|---|---|---|---|
| | A | B | C |
| M300 | 100 | 100 | 100 |
| M344 | 92 | 93 | 90 |
| M75 | 45 | 40 | 50 |
| 19A211 | 0 | 0 | 0 |

Immunoblot experiments on tumor extracts show that M75, M300 and M344 monoclonal antibodies react with the same components with a lower reactivity for M75 as expected. The antigen resides in a high molecular weight component in the range of 300,000 $M_r$ with a pI 9.5, and a lower molecular weight component of 62,000 $M_r$ and pI 6.5. Pretreatment of the sample with RNase or alkylating agents (N-Ethylmaleimide and Iodoacetamide) did not change the migration pattern of the high molecular weight form.

To determine the biochemical specificity of M344 binding, ammonix- extracted proteins (100 μg/sample) from three urothelium and six bladder tumors (4 reactive and 2 negative by immunoperoxidase staining) were electropheresed and transferred simultaneously onto the same paper and reacted with M344 antibody. This experiment confirmed the specificity of M344, which did not react with the normal urothelial extracts and those of two high grade, high stage bladder tumors, but did react with antigen from four superficial tumors. All four positive samples showed the high molecular form, although at a low level in sample 5, but in only two samples was the 62 Kda protein detected.

Biochemical studies of the antigen detected by monoclonal antibody 19A211 revealed that this antigen was detected in immunoblot from extracts of the tumors. The protein can be detected with very high sensitivity on several tumors and was not detected or was very weak on the urothelium tested that were found to be slightly positive by immunoperoxidase staining of the sections. The two-dimensional analysis of the protein detected by the antibody showed several subunits with different pIs and a molecular weight between 90 and 100 kilodaltons under reducing conditions.

While immunohistology data confirms a high degree of heterogeneity of expression within individual tumors, immunoblot analysis of extracts of a limited number of tumors suggest polymorphism at a molecular level.

EXAMPLE 4

Combined use of M344 and 19A211 antibodies for the detection of superficial papillary bladder tumors.

The results of studies of M344 and 19A211 antibodies show that these two distinct antigens are preferentially expressed on superficial papillary tumors of the human urinary bladder. Table 7 presents the results of staining of superficial bladder tumors in which the results of diagnostic urine cytology tests were available immediately before the removal of the bladder tumor.

TABLE 7

Reactivity of M344 and/or 19A211 monoclonal antibodies on papillary superficial (Ta) bladder tumors according to results of urine cytology tests

| Urine cytology | Number of specimen tested | Number reacting with | | |
|---|---|---|---|---|
| | | M344 | 19A211 | one or both |
| Positive | 4 | 2 | 3 | 3 |
| Negative | 28 | 20(70%) | 19(68%) | 25(90%) |

In only 4/32 (15%) of the instances was the urine cytology positive and predictive of the presence of the tumors. In the 28 cases where the urine cytology test did not predict the presence of the tumors, 25/28 (90%) of the tumors were reacting with either one or both monoclonal antibodies M344 and 19A211. This strongly suggests that the combination of these two antibodies could very significantly improve the detection of this bladder tumor type.

The antibodies can also be used in multiparameter flow cytometry studies to label bladder tumor cells. In these instances, 19A211 and M344 antibodies are able to distinguish papillary bladder tumor cells with a normal diploid DNA pattern from normal urothelial cells with a similar DNA pattern. This is in contrast with other antibody against a normal differentiation antigens of the urothelium T16 and OM5 which react with both cell types.

EXAMPLE 5

Test kit preparation

The ascites fluid from hybridomas M75, M300, M344 and 19A211 were purified on Pharmacia Mono Q columns as described in Examples 1 and 2. The protein fraction obtained was diluted in a carbonate buffer (1.59 g Na$_2$CO$_3$, 2.93 g NaHCO$_3$ and 0.2 g NaN$_3$ q.s. one liter with water to a concentration of 50 mg/ml and a 0.2 ml aliquot was added to each well of a Dynatech ® substrate plate. Following this addition, the plate was covered tightly with parafilm and incubated at 2° to 8° C. for 16 to 22 hours. Following the incubation, the fluid in each well was removed and the tray wells were washed three times with BPS-Tween ® (8.0 g NaCl, 0.2 g KH$_2$PO$_4$, 2.9 g Na$_2$HPO$_4$.12H$_2$O, 0.2 g KCl and 0.5 ml Tween ® 20 diluted in water to make one liter of solution). These tray wells coated with monoclonal antibodies M75, M300, M344 and 19A211 form the solid phase to be used in the subject test kit.

The other ingredients in the kit are the anti-human IgG/enzyme conjugate, the PBS-Tween® solution, the substrate for the enzyme and the controls.

These other materials would generally be included in a kit for convenience and standardization. The control substances used in the subject test kit are human serum to which differing amounts of lyophilized heat-aggregated IgG has been added.

What is claimed is:

1. The hybridoma which secretes monoclonal antibodies which specifically reacts with extracts from superficial papillary bladder tumor of the human urinary bladder and which does not substantially cross react with normal human non-urothelial cells nor with non-urothelial tumor cells, said hybridoma being selected from the group consisting of ATCC HB 9678 and ATCC HB 9679.

2. The monoclonal antibody produced by the hybridoma cell line ATCC HB 9678 which specifically reacts with extracts from superficial papillary bladder tumor of the human urinary bladder and which does not substantially cross react with normal human urothelial cells, with normal human non-urothelial cells nor with non-urothelial tumor cells.

3. The monoclonal antibody produced by the hybridoma cell line ATCC HB 9679 which specifically reacts with extracts from superficial papillary bladder tumor of the human urinary bladder, which cross react with limited cell fractions of normal human urothelial cells and which does not substantially cross react with normal human non-urothelial cells nor with non-urothelial tumor cells except for skin condylomas.

* * * * *